United States Patent [19]

Tolles

[11] 4,432,642
[45] Feb. 21, 1984

[54] NEPHELOMETER

[76] Inventor: Walter E. Tolles, Lee Hwy., Fairfield, Va. 24435

[21] Appl. No.: 309,034

[22] Filed: Oct. 6, 1981

[51] Int. Cl.³ ............................................. G01N 21/03
[52] U.S. Cl. .................................... 356/246; 356/338
[58] Field of Search ............... 356/246, 338, 440, 133, 356/135; 250/564, 574, 576, 225; 350/536

[56] References Cited

U.S. PATENT DOCUMENTS 4,027,979  6/1977  Komarniski ................. 356/440 X
4,060,388  11/1977  Rapp et al. ..................... 356/246 X Primary Examiner—William L. Sikes
Assistant Examiner—Matthew W. Koren
Attorney, Agent, or Firm—B. P. Fishburne, Jr.

[57] ABSTRACT

A nephelometer is disclosed which employs immersion optics and conformable optical couplers between components to minimize scattered background light. A multi-compartment micro volume specimen holder employs a cover having integral spacer knees which assure a precision length optical path. The device has the ability to collect small forward-angle scattered light with maximum efficiency and sensitivity. Light pipes are employed to remove a glass-air interface to a remote point where scattering is of much less importance and to act as an axicon for the compact collection of angularly scattered light.

4 Claims, 6 Drawing Figures

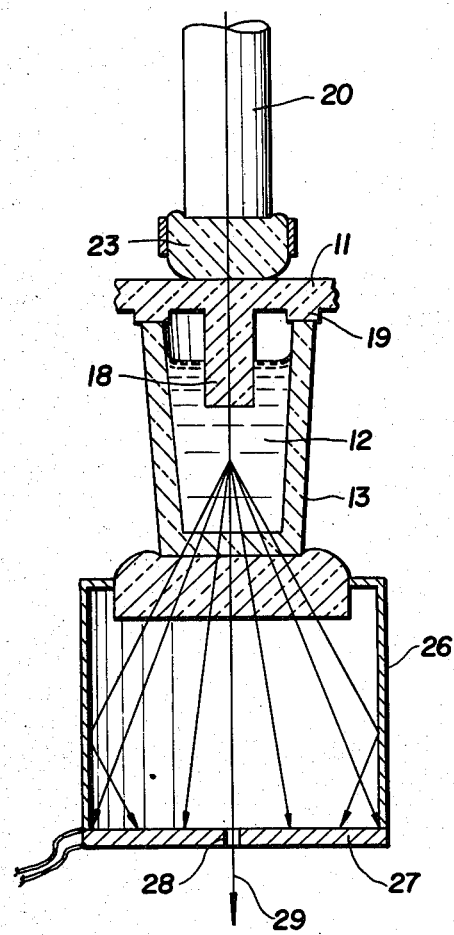

NEPHELOMETER

CROSS-REFERENCE TO RELATED APPLICATION

This application contains some common subject matter with copending application Ser. No. 06/309,035, filed Oct. 6, 1981 for CONFORMABLE OPTICAL COUPLERS.

BACKGROUND OF THE INVENTION

Precision work with nephelometers or turbidimeters is hampered by scattered light along the light path of the instrument caused by interfacial reflections wherever open surfaces exist in the system, such as an air-dielectric boundary. Certain techniques are well known in the optical science to deal with scattered light and background light in general; in particular instances, the techniques include the use of immersion optics, light piping and refractive index matching devices.

One object of this invention is to employ some of these techniques collectively or singly in an improved nephelometer of the type having a multi micro volume specimen well structure equipped with a cover to avoid evaporation and cross contamination of wells.

A very important feature of the invention is the provision on the cover of integral depending immersion light pipes or pins which project into the liquid specimens contained in the micro volume wells and shorter spacer knees on the bottom of the cover which contact the top face of the well structure to establish and maintain a precision length light path.

In addition to these features, the nephelometer employs light pipes and comformable optical couplers to eliminate open optical surfaces or to remove such surfaces to remote locations where the scattering effect is substantially reduced.

Other features and advantages of the invention will appear to those skilled in the art during the course of the following detailed description.

BRIEF DESCRIPTION OF THE DRAWINGS

FIG. 6 is a partly schematic view of a nephelometer in accordance with the present invention.

DETAILED DESCRIPTION

Figure 1:
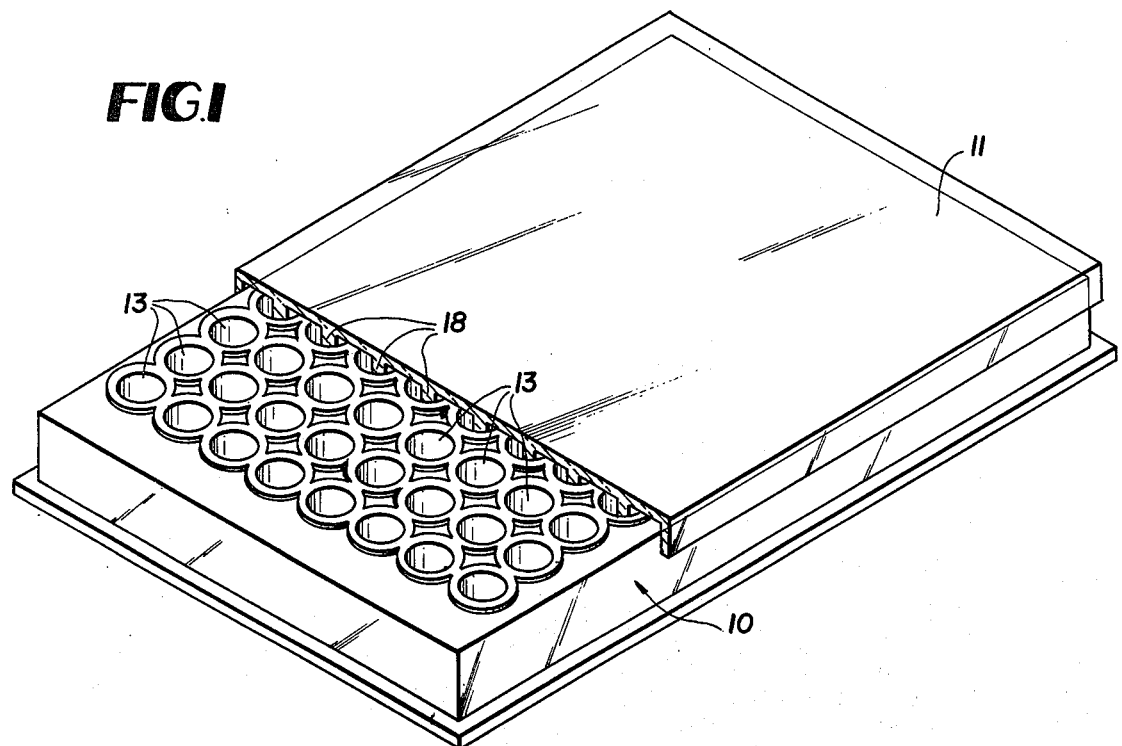
FIG. 1 is a perspective view, partly in section, of a covered plate containing multi micro volume wells according to the present invention.
Figure 3:
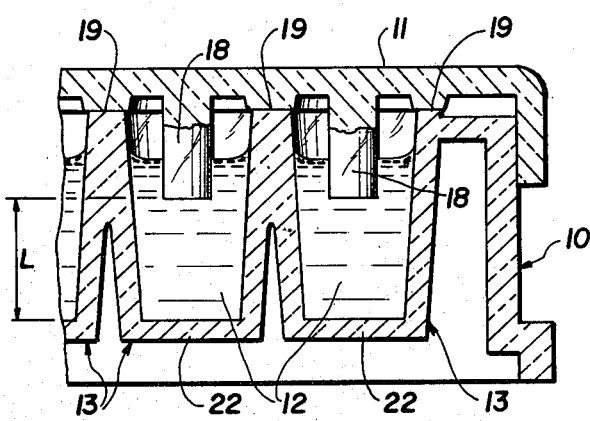
FIG. 3 is a similar section taken through the specimen holder of FIG. 1 according to the invention.

Referring to the drawings in detail wherein like numerals designate like parts, a multi micro volume well liquid specimen holder 10 and removable cover 11 are shown in FIGS. 1 and 3 of the drawings in accordance with a primary feature of the invention. The micro volume specimens 12 contained in the specimen wells 13 of holder 10 are about 1/50 to 1/250 the volume of conventional nephelometers, and herein resides one of the most important efficiency and convenience aspects of the invention. The purpose of the specimen holder cover 11 is to inhibit evaporation and cross contamination of the specimens in the micro volume wells 13.

Figure 2:
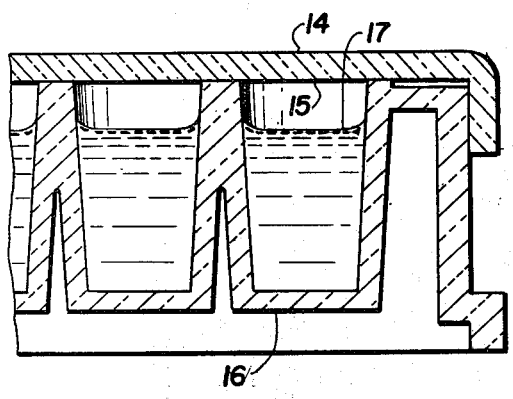
FIG. 2 is an enlarged fragmentary vertical section taken through a covered multi well specimen holder according to the prior art.
Figure 4:
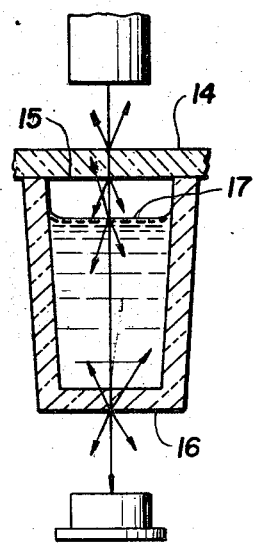
FIG. 4 is a partly schematic fragmentary section depicting the light path of a nephelometer in accordance with the prior art.

In the prior art, FIGS. 2 and 4, separated or open optical surfaces 14, 15 and 16 are allowed to exist in the system, as well as the open liquid surface 17 of each well specimen, these latter surfaces sometimes being other than flat, as is well known, where the well volumes are very small. Wherever these open surfaces exist, interfacial reflections and light scattering are created in addition to normal light refraction as between elements having different indices of refraction, such as air and glass, liquid and glass, or air and liquid. Additionally, in the prior art, there is not always a precision length optical path through the nephelometer. The depth of liquid in the specimen wells may vary from well-to-well changing the characteristics of the optical path for those wells. The invention deals with all of these problems in the prior art in a very effective and simple manner, now to be described.

Figure 5:
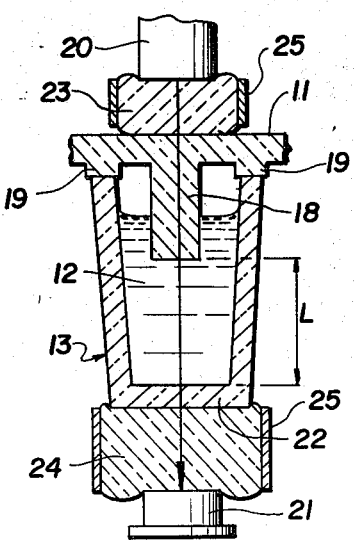
FIG. 5 is a similar view in cross section taken through a nephelometer constructed in accordance with the invention.

Referring to FIGS. 3 and 5 showing the invention, the specimen holder cover 11 has integrally formed thereon a plurality of identical depending immersion light pipes or pins 18, one for each specimen well 13 centrally and coaxially located therein. The depending small light pipes 18 are partly immersed in the liquid specimens 12 contained in the wells to eliminate open surfaces and air gaps in the optical path through the specimen holder.

Additionally, precision spacer knees 19 are integrally formed on the bottom face of cover 11 and engage the top surface of holder 10 to establish and maintain a precision length light path L through the specimen wells 13, as indicated in FIG. 5. In a practical embodiment, the specimen holder 10 and its cover 11 are die molded from clear plastics for the sake of economy.

As shown in FIG. 5, the nephelometer may include an upper light pipe element 20 and a lower light pipe or detector 21 spaced, respectively, from the top face of cover 11 and the bottom wall 22 of specimen chamber 13. Conformable optical couplers 23 and 24 of the type described in the above-referenced copending application are interposed between the elements 11 and 20 and 21 and 22 to avoid using optical cement or optical grease between these elements, which is awkward, and in the case of cement would require permanent attachment of the components, precluding rapid series of observations by clamping or unclamping a light source and detector, as in an automated high volume system.

As described in the copending application, the conformable optical couplers 23 and 24 may comprise clear elastomer bodies such as General Electric silicone elastomer. The couplers can be compressed by a constrictive ring 25 or the like to expand them into firm shape conforming engagement with the elements 11 and 20 and 21 and 22. The optical couplers, when employed, are readily separable from the assembly.

FIG. 6 depicts the micro volume specimen well 13, the improved cover 11 with spacer knees 19, the upper light pipe element 20 and the described upper optical coupler 23. Below the well 13, a scattered light pipe 26 is schematically shown at the bottom of which is disposed a detector element 27, having an aperture 28 for the central emergent light beam 29.

The nephelometer, as described in connection with FIG. 6, has the ability to collect small forward-angle scattered light with high efficiency and sensitivity. An infinity sink for the main light beam is provided instead of obstacle deflectors or Raman traps. By virtue of the light pipes or pins 18, immersion optical coupling to the fluid specimen 12 is provided. The light pipe 26 of the nephelometer acts as an axicon for the compact collection of angularly scattered light. The "healing" of poor optical surfaces, such as molded surfaces, is provided for. The use of light pipe 20 in the system moves the cover to air interface to a distance where scattering is much less important. The employment of conformable optical couplings between solid components further reduces scattering and enhances convenience of assembly and use.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. In a nephelometer, a fluid specimen holder having at least one micro-volume specimen well including a bottom wall and being open at its top, a cover for the specimen holder overlying the well and having an attached depending light pipe element projecting into the well and being immersed in a fluid specimen contained by the well, precision spacer means on the bottom of the cover abutting a top surface of the specimen holder and establishing and maintaining a precision length light path through the nephelometer between the bottom of the light pipe element and said bottom wall, an additional light pipe means spaced from said cover and said bottom wall in coaxial relationship with said well and light pipe element, and conformable optical coupler means disposed between said additional light pipe means and said cover and bottom wall.

2. In a nephelometer as defined in claim 1, and said conformable optical coupler means including an optical elastomer held in firm conforming engagement with the light pipe means, cover and bottom wall.

3. In a nephelometer as defined in claim 2, and the nephelometer additionally comprising a scattered light collector means and light detector means downstream from said well and conformable optical coupler means.

4. A nephelometer comprising a shallow unitary fluid specimen holder having a multiplicity of micro-volume specimen wells disposed in a common plane, said wells having bottom walls in a common plane and having open tops in a common plane parallel to the plane occupied by the bottom walls of the wells, the wells of the specimen holder being separated by connected side walls which are shared by adjacent specimen wells of said multiplicity, a cover for the specimen holder common to and spanning the open tops of all of said wells, precision surfaces on the bottom of the cover in a common plane and abutting opposing precision surfaces on the top of the specimen holder in a common parallel plane to establish and maintain precision light paths through the nephelometer, a light pipe pin element dependingly and integrally formed on the cover adjacent to each specimen well and being centrally and coaxially located with respect to each well, the light pipe pin elements projecting through the open tops of the wells and having at least their lower end portions immersed in fluid specimens contained in the wells, additional coaxial light pipe elements spaced from the top of the cover and from the bottom walls of said wells, and conformable optical coupler elements disposed between the opposing ends of said additional light pipe elements and the top of the cover and said bottom walls, the optical coupler elements being formed of an optical elastomer held in firm conforming contact with the ends of the additional light pipe elements and the top of the cover and said bottom walls.

* * * * *